United States Patent
Pan

(10) Patent No.: US 8,948,846 B2
(45) Date of Patent: Feb. 3, 2015

(54) OPTICAL COHERENCE TOMOGRAPHY SYSTEMS AND METHODS

(75) Inventor: Yingtian Pan, Stony Brook, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 767 days.

(21) Appl. No.: 12/678,377

(22) PCT Filed: Sep. 18, 2008

(86) PCT No.: PCT/US2008/076893
§ 371 (c)(1),
(2), (4) Date: Jun. 24, 2010

(87) PCT Pub. No.: WO2009/039303
PCT Pub. Date: Mar. 26, 2009

(65) Prior Publication Data
US 2010/0280315 A1    Nov. 4, 2010

Related U.S. Application Data

(60) Provisional application No. 60/973,571, filed on Sep. 19, 2007.

(51) Int. Cl.
*A61B 5/05* (2006.01)
*A61B 5/00* (2006.01)
*G01N 21/47* (2006.01)
*G02B 3/00* (2006.01)
*G02B 13/22* (2006.01)

(52) U.S. Cl.
CPC ............. *A61B 5/6852* (2013.01); *A61B 5/0066* (2013.01); *G01N 21/4795* (2013.01); *G02B 3/0087* (2013.01); *G02B 13/22* (2013.01)

USPC .......... 600/425; 600/407; 600/409; 356/479; 356/497

(58) Field of Classification Search
None
See application file for complete search history.

(56) References Cited

U.S. PATENT DOCUMENTS

| | | | |
|---|---|---|---|
| 6,680,780 B1 * | 1/2004 | Fee ............................... | 356/498 |
| 7,187,494 B2 * | 3/2007 | Nishiwaki et al. ............ | 359/388 |
| 7,231,243 B2 * | 6/2007 | Tearney et al. ................ | 600/407 |
| 8,032,200 B2 * | 10/2011 | Tearney et al. ............... | 600/407 |
| 8,149,418 B2 * | 4/2012 | Tearney et al. ............... | 356/479 |

(Continued)

OTHER PUBLICATIONS

Chou, P.C. et al., "Reconfigurable time-domain spectral shaping of an optical pulse stretched by a fiber Bragg grating," Opt. Lett. 25, pp. 524-526 (2000).

(Continued)

*Primary Examiner* — Nicholas Evoy
(74) *Attorney, Agent, or Firm* — Fish & Richardson P.C.

(57) ABSTRACT

In general, in one aspect, the invention features a method that includes using an optical coherence tomography system to acquire a plurality of frames of a sample where each frame includes optical information about the composition of the sample through a section of the sample. The method further includes averaging over two or more of the frames to provide an image of the section of the sample where successive frames of the two or more frames are acquired with a time lapse of 0.05-0.7 seconds. Embodiments of the method may have unique advantages for endoscopic subcellular imaging. For example, they can enable subcellular imaging with low-NA optics (e.g., NA=0.25 or less) while providing morphological imaging of the underlying tissue up to 0.6 mm without focal tracking.

26 Claims, 13 Drawing Sheets

(56) References Cited

U.S. PATENT DOCUMENTS

| | | | | |
|---|---|---|---|---|
| 8,150,496 | B2* | 4/2012 | Tearney et al. | 600/425 |
| 8,174,702 | B2* | 5/2012 | Tearney et al. | 356/479 |
| 8,275,449 | B2* | 9/2012 | White et al. | 600/431 |
| 8,369,669 | B2* | 2/2013 | Bouma et al. | 385/116 |
| 8,447,526 | B2* | 5/2013 | Weng et al. | 702/19 |
| 8,559,012 | B2* | 10/2013 | Tearney et al. | 356/479 |
| 8,676,013 | B2* | 3/2014 | Bouma et al. | 385/116 |
| 8,760,663 | B2* | 6/2014 | Tearney et al. | 356/479 |
| 8,838,213 | B2* | 9/2014 | Tearney et al. | 600/478 |
| 2002/0183601 | A1* | 12/2002 | Tearney et al. | 600/310 |
| 2003/0103212 | A1* | 6/2003 | Westphal et al. | 356/479 |
| 2003/0142934 | A1* | 7/2003 | Pan et al. | 385/116 |
| 2007/0015135 | A1* | 1/2007 | Weng et al. | 435/4 |
| 2007/0073162 | A1* | 3/2007 | Tearney et al. | 600/476 |
| 2007/0077045 | A1 | 4/2007 | Kato | |
| 2007/0238954 | A1* | 10/2007 | White et al. | 600/407 |
| 2009/0219544 | A1* | 9/2009 | Joo et al. | 356/456 |
| 2010/0280315 | A1* | 11/2010 | Pan | 600/109 |
| 2012/0022381 | A1* | 1/2012 | Tearney et al. | 600/479 |
| 2012/0307035 | A1* | 12/2012 | Yaqoob et al. | 348/79 |
| 2013/0083981 | A1* | 4/2013 | White et al. | 382/128 |
| 2013/0088568 | A1* | 4/2013 | Nolte | 348/40 |
| 2013/0096017 | A1* | 4/2013 | Nolte et al. | 506/8 |
| 2013/0144151 | A1* | 6/2013 | Nolte et al. | 600/407 |

OTHER PUBLICATIONS

Drexler, W. et al., In vivo ultrahigh-resolution optical coherence tomography, Opt. Let 24, pp. 1221-1223 (1999).

Drexler, Wolfgang, "Ultrahigh-resolution optical coherence tomography", Journal of Biomedical Optics 9, pp. 47-74 (2004).

Kowalevicz, Andrew et al., "Ultrahigh resolution optical coherence tomography using a superluminescent light source", Optics Express, vol. 10, Issue 7, pp. 349-353 (Apr. 2, 2002).

W. Piyawattanametha et al., "Two-Dimension Endoscopic MEMS scanner for High Resolution Optical Coherence Tomography", Lasers and Electro-Optics, CLEO Conference, vol. 1, pp. 1449-1451 (May 16, 2004).

Wagenblast, Philipp C., et al. "Ultrahigh-resolution optical coherence tomography with a diode-pumped broadband $Cr^{3+}$: LiCAF laser", Optics Express 12, pp. 3257-3263 (2004).

Xie, Q. et al., "Dispersion compensation in high-speed optical coherence tomography using acousto-optic modulation", Appl. Opt., 44, pp. 4272-4280 (2005).

Int'l. Search Report and Written Opinion dated Feb. 24, 2009, corresponding to Int'l. Appln. No. PCT/US2008/076893.

* cited by examiner

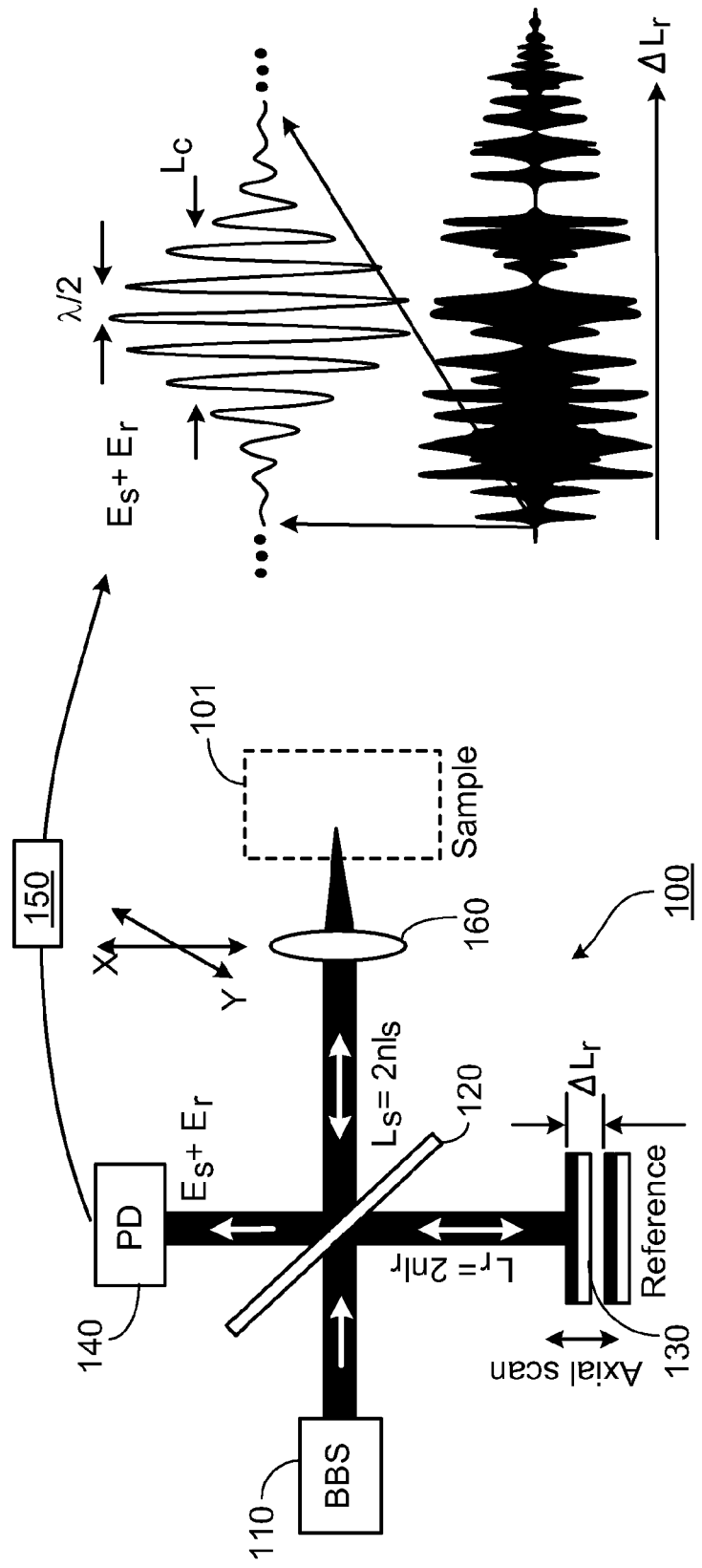

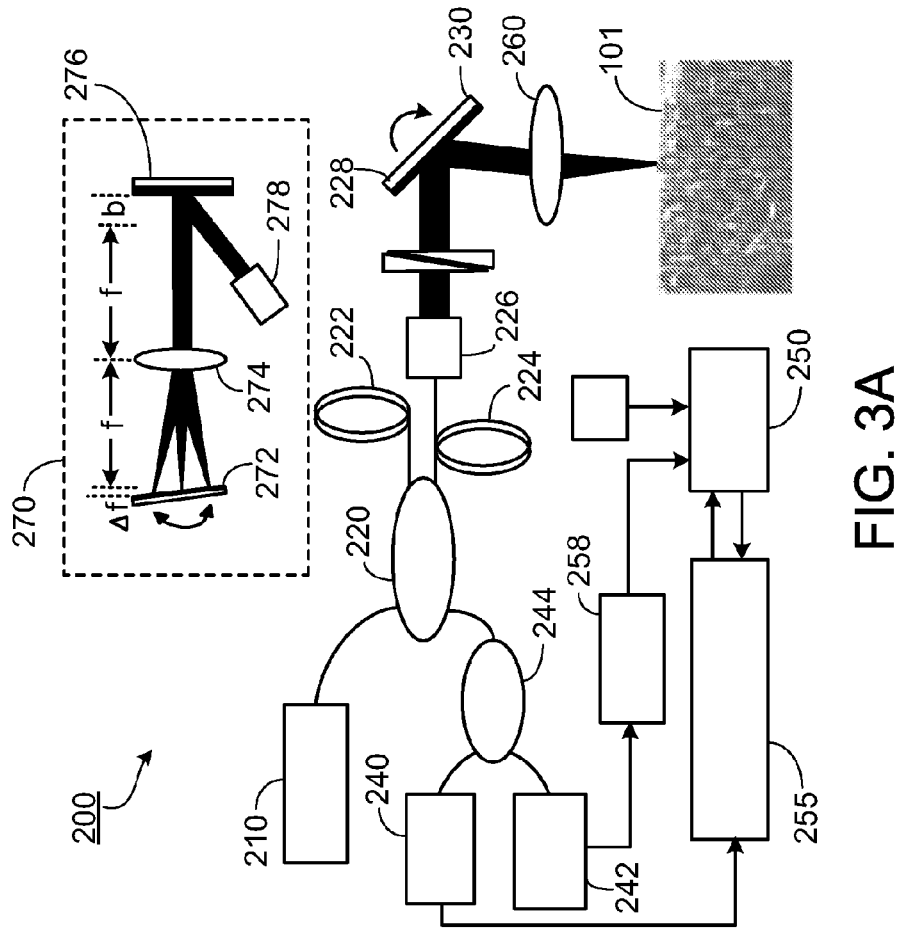
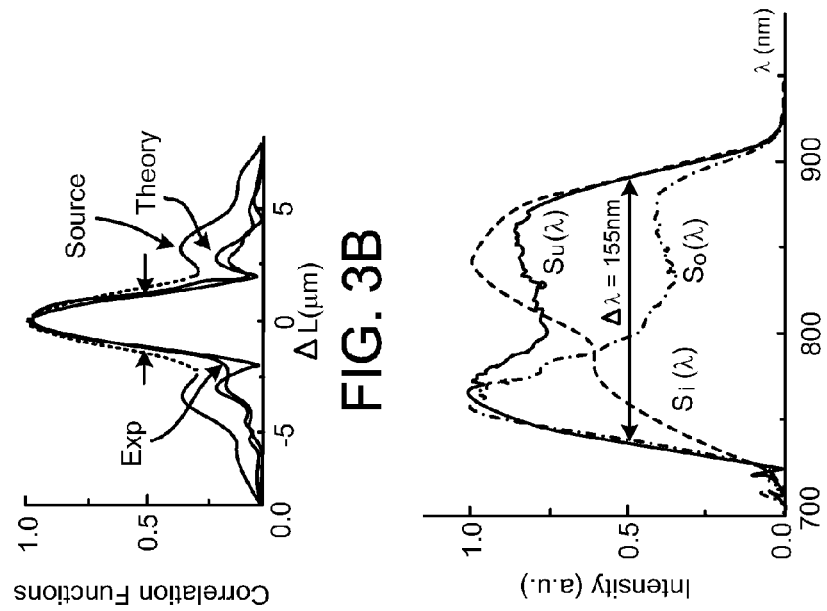
FIG. 3A
FIG. 3B
FIG. 3C

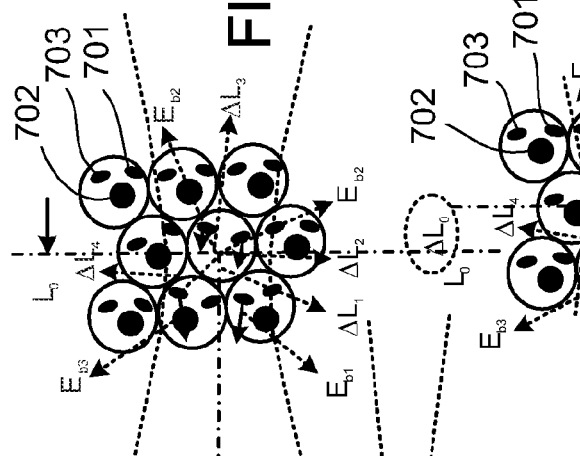
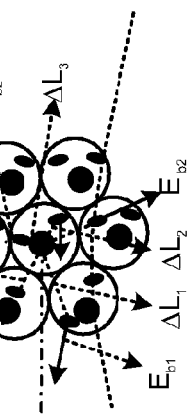
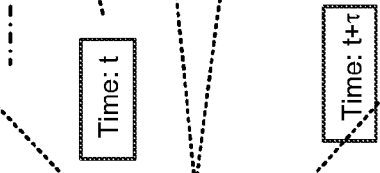
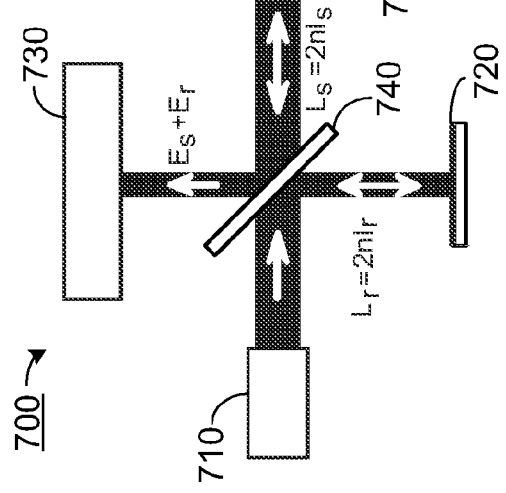
FIG. 6A
FIG. 6B
FIG. 6C

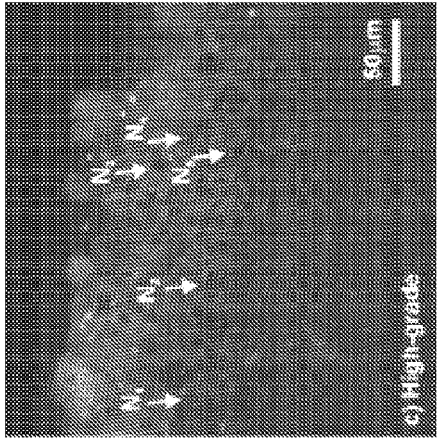
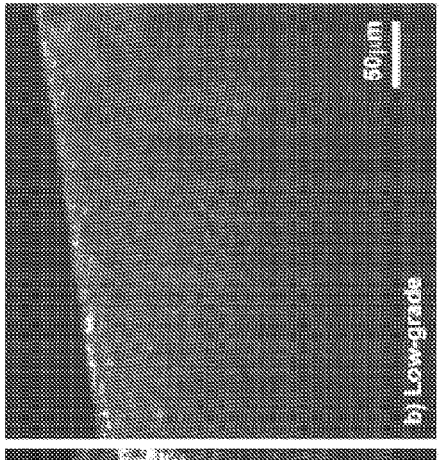
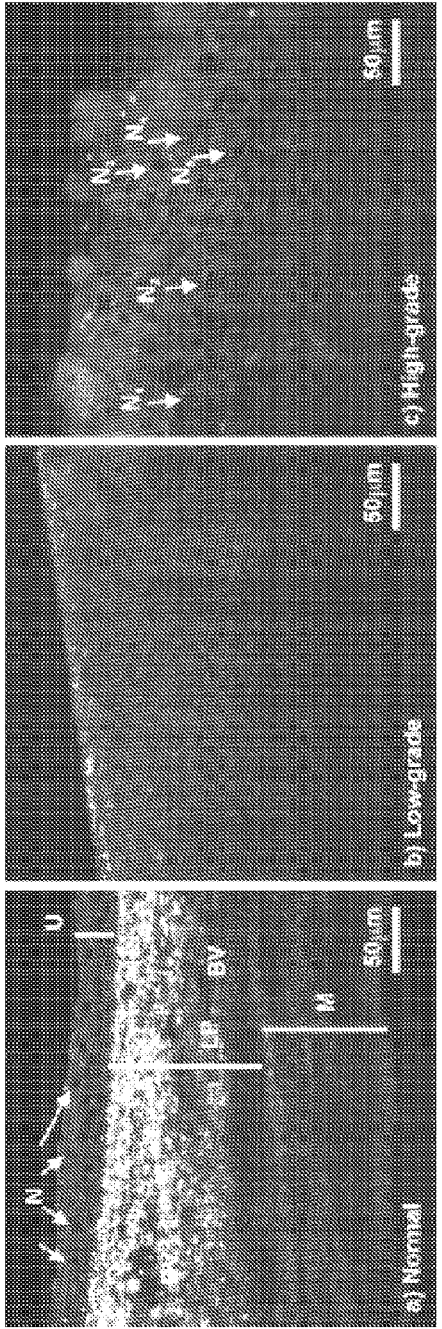
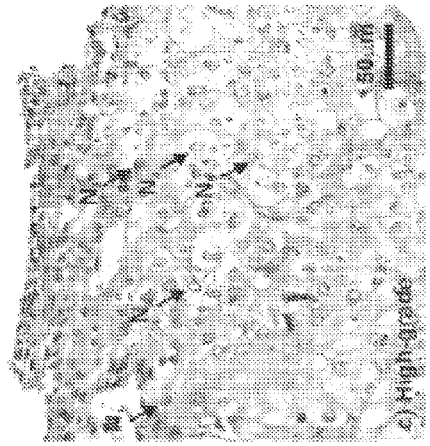
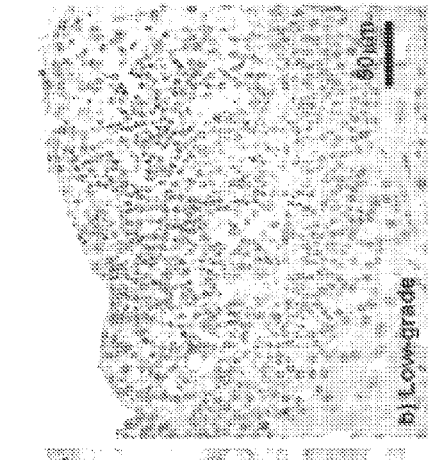
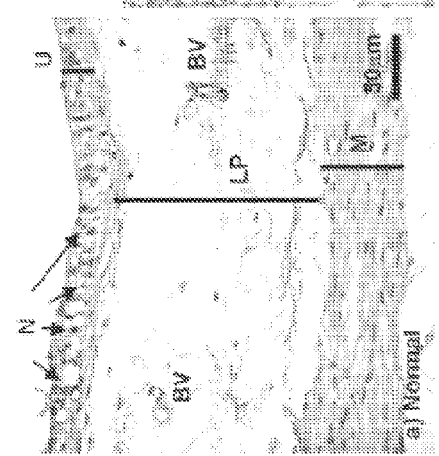

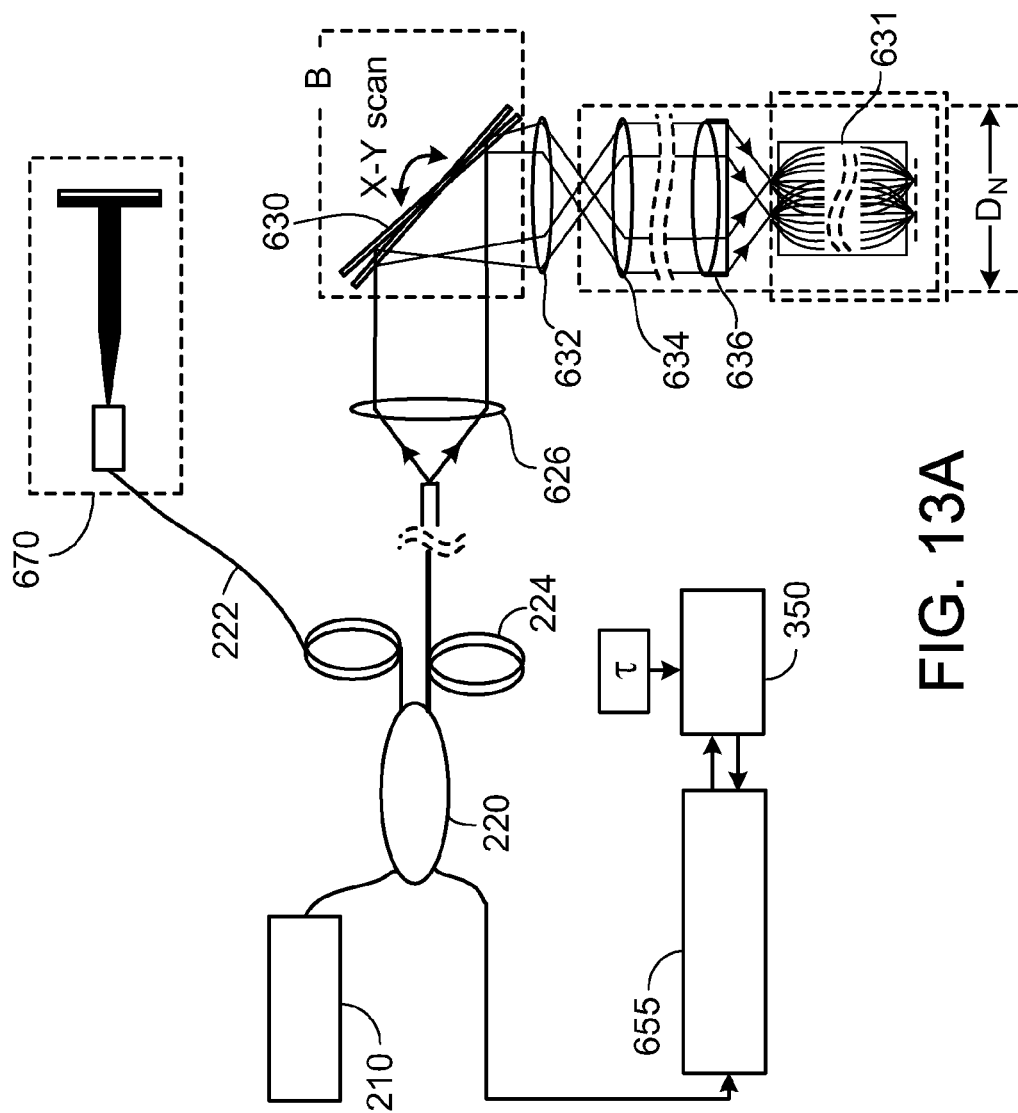

OPTICAL COHERENCE TOMOGRAPHY SYSTEMS AND METHODS

CROSS-REFERENCE TO RELATED APPLICATIONS

This application claims benefit of Provisional Patent Application No. 60/973,571, entitled "OPTICAL COHERENCE TOMOGRAPHY SYSTEMS AND METHODS," filed on Sep. 19, 2007, the entire contents of which are incorporated herein by reference.

FIELD OF INVENTION

This invention relates to optical coherence tomography and laser scanning endoscopy.

BACKGROUND

Most biological tissue, such as urinary bladder tissue, is optically turbid and not only absorbs but also scatters light in the optical and near-infrared wavelength range. Light scattering can cause severely degraded image contrast and reduced spatial resolution; therefore, advanced optical imaging techniques such as optical coherence tomography (OCT) and/or confocal microscopy can be used to effectively reject multiple scattering and thus reconstruct an image of the tissue image. For many applications, however, OCT images are correlated with histology to differentiate different tissue types. For example, histological studies are typically used in conjunction with OCT images to identify the morphology of bladder tissue, including morphological changes induced by, e.g., urothelial carcinogenesis.

SUMMARY

In general, in a first aspect, the invention features methods that include using an optical coherence tomography system to acquire a plurality of frames of a sample where each frame includes optical information about the composition of the sample through a section of the sample. The method further includes averaging over two or more of the frames to provide an image of the section of the sample where successive frames of the two or more frames are acquired with a time lapse of about 0.05-0.70 seconds (e.g., 0.04, 0.05, 0.10, 0.25, 0.50, 0.60, 0.70 or 0.71 seconds).

Embodiments of the method can include one or more of the following features. For example, the time lapse between successive frames can be about 0.1 seconds or more (e.g., about 0.5 seconds). The time lapse between successive frames can be about 0.5 seconds or less (e.g., about 0.4 seconds or less (e.g., as little as about 0.1 seconds). In some embodiments, the time lapse between successive frames is in a range from about 0.1 seconds to 0.4 seconds (e.g., 0.1 s, 0.2 s, 0.3 s, or 0.4 s).

The averaging can be over three or more frames to provide the image (e.g., over four or more frames, over five or more frames, or over six or more frames).

The tissue sample can be within a living organism while the frames are acquired; within a tissue of an organism deceased so recently that the tissue retains at least some of the motion normally seen in tissue within a living organism; or within a tissue maintained ex vivo. The time lapse between successive frames can be selected based on motion of the tissue sample. The time lapse can be selected to reduce the effects of speckle in the image.

Acquiring each frame can include directing test radiation onto the sample, collecting test radiation scattered by the sample, and combining the collected test radiation with reference radiation, the test and reference radiation being produced by a common source. The common source can be a laser or a light emitting diode, for example. The test and reference radiation can be directed along different paths prior to being combined, and an optical path length difference between at least some of the test and reference radiation is zero. The test and reference radiation can be low-coherence radiation. In some embodiments, the test and reference radiation is broadband radiation. Directing the test radiation onto the sample can include focusing the test radiation onto the sample. The test radiation can be focused using an objective lens consisting of an achromatic doublet. The test and reference radiation can be directed along the different paths using an interferometer (e.g., a Michelson interferometer). Acquiring each frame can include varying an optical path length of the reference radiation path. The optical path length of the test radiation can be held constant while the optical path length of the test radiation is varied. Acquiring each frame can include scanning the test radiation across a portion of the sample and varying the optical path length of the reference radiation path for each of a plurality of locations across the portion of the sample. The test radiation can be scanned using a MEMS device.

In some embodiments, the test radiation is delivered to the sample using an endoscope. The sample can be an in vivo sample. The in vivo sample can be from a human subject.

In certain embodiments, acquiring the frames includes amplifying an interference signal corresponding to detected combined test and reference radiation, wherein the interference signal is amplified using a non-logarithmic scale. The non-logarithmic scale can be a linear scale. The linear-scale amplitude demodulation can be incompletely demodulated sufficient so that the remaining ripples promote frame averaging to reduce speckle noise. It is believed that time-varying micromotion can lead to time-varying phase changes of the speckles, which is why time-lapse frame averaging, termed as time-lapse ultrahigh-resolution OCT (TL-uOCT) can effectively reduce speckles to uncover nuclear morphology. The amplitude of the interference signal can be amplified at a frequency, $f_D$, where $f_D$ is a heterodyne frequency between sample light and reference light of the optical coherence tomography system. The interference signal can be filtered using a frequency bandpass filter that passes $f_D$ prior to amplification.

In general, in a further aspect, the invention features a system that includes an interferometer configured to receive input light from a source and derive sample light and reference light from the input light, direct the sample light to a sample and direct the reference light to a reference object, and to combine sample light reflected from the sample with reference light reflected from the reference object to produce output light. The system also includes a detector positioned to receive the output light and produce interference signals that include information about an optical path difference between the sample light and the reference light, and an electronics module configured to receive the interference signals from the detector and acquire a plurality of frames of a sample, average over two or more of the frames to provide an image of a section of the sample, where each frame includes optical information about the composition of the sample through a section of the sample, and successive frames of the two or more frames are acquired with a time lapse of 0.05-0.7 s. Embodiments of the system can include one or more of the features listed above.

In general, in another aspect, the invention features a system that includes an interferometer configured to receive input light from a source and derive sample light and reference light from the input light, direct the sample light to a sample and direct the reference light to a reference object, and to combine sample light reflected from the sample with reference light reflected from the reference object to produce output light. The system also includes a detector positioned to receive the output light and produce interference signals that includes information about an optical path difference between the sample light and the reference light, and an electronics module configured to receive the interference signals and produce an image of a section of the sample based on the interference signals, wherein the image has an axial resolution of 2 μm or less. Embodiments of the system can include one or more of the features listed above.

Among other advantages, embodiments of the invention include optical coherence tomography systems and methods that provide extremely high axial resolution for biological samples. For example, in certain embodiments, features as small as 1.8 μm along the axial direction can be resolved using the systems and methods disclosed herein. Accordingly, the optical coherence tomography systems and methods can be used to resolve subcellular features in biological samples (e.g., bladder tissue). As a result, the optical coherence tomography systems and methods can be used to diagnose diseases that manifest as changes in the appearance of subcellular features, such as nuclear size and/or shape. Examples of such diseases include certain cancers, such as transitional cell carcinoma (e.g., in bladder cancer). Accordingly, the optical coherence tomography systems and methods can be used in the diagnosis of certain cancers.

The techniques can provide subcellular imaging of small cells, e.g., epithelium. For example, the techniques can be used to resolve nuclear morphology of small epithelial cells using TL-uOCT. Without wishing to be bound by theory, it is believed that this form of OCT takes advantage of local (e.g., intracellular) micro motion to reduce speckle noise that can prevent ultrahigh-resolution OCT to resolve subcellular details of epithelium. Accordingly, the techniques can be used in the diagnosis and grading of cancers.

TL-uOCT can provide subcellular imaging at a focal zone (e.g., up to 60 μm) and, at the same time, provide high-resolution imaging of underlying morphology. This can be achieved without focal tracking.

Accordingly, in some embodiments, the optical coherence tomography systems and methods can be implemented using an endoscope, allowing for in vivo studies of internal organs.

Other features and advantages will be apparent from the description and drawings, and from the claims.

BRIEF DESCRIPTION OF THE FIGURES

FIG. 1 is a schematic diagram of a Time Domain (TD) Optical Coherence Tomography (OCT) system.

FIG. 2 is a plot of detected intensity as a function of scan position (lower plot), as well as an expanded portion of the plot showing an interference signal (upper plot).

FIG. 3A is a schematic diagram of an embodiment of a TD TL-uOCT system.

FIG. 3B is a plot showing example spectra for sample light, reference light, and output light for an implementation of the TD-OCT system shown in FIG. 3A.

FIG. 3C is a plot showing correlation functions for the implementation of the TD-uOCT system shown in FIG. 3A.

FIG. 6A is a schematic diagram of a Spectral Domain (SD) Optical Coherence Tomography (OCT) system.

FIGS. 6B and 6C are schematic diagrams showing relative cell positions at times t and t+τ, respectively. The global motion of the tissue (or sample arm) which can be approximated as a translation $\Delta L_0$ can be compensated by $L_r$ or image registration. The local motion of the intracellular organelles as highlighted by $\Delta L_1, \ldots, \Delta L_4$ causes speckle phase change, if averaged, can effectively reduce speckle noise.

FIGS. 9A-9C are time lapse frame averages uOCT images of three different samples of living mouse bladder ex vivo.

FIGS. 10A-10C are respective histological microscope images of the samples shown in FIGS. 9A-9C.

FIG. 13A is a schematic diagram of an embodiment of a needle-based TD-uOCT system.

FIG. 13B is a perspective view of a micro-electromechanical system (MEMS) mirror.

DETAILED DESCRIPTION

Figure 4:
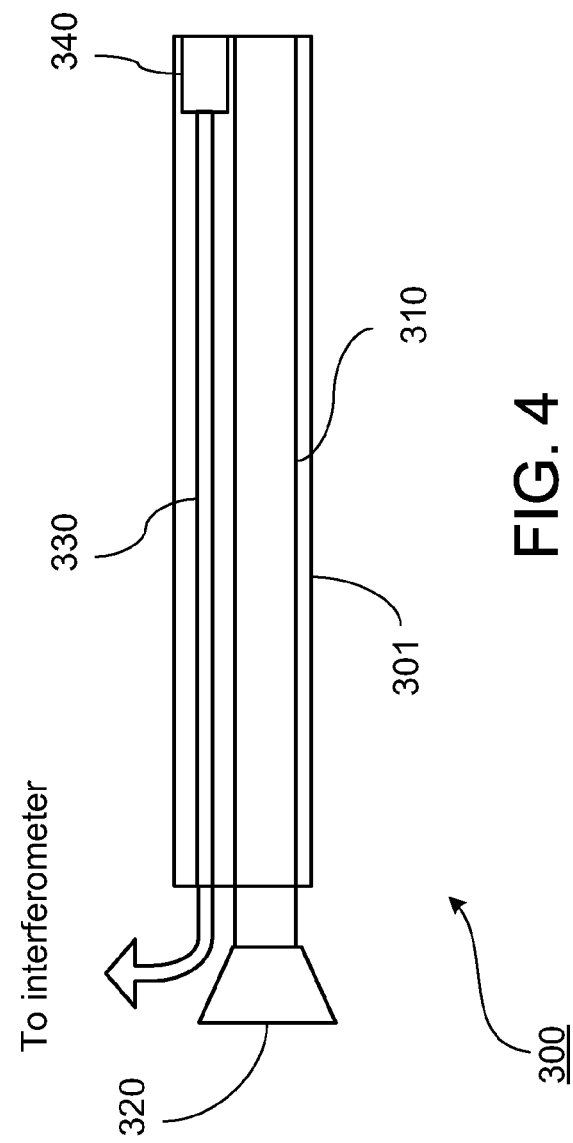
FIG. 4 is a schematic diagram of an endoscope for use with an OCT system.

Optical coherence tomography (OCT) uses coherence gating to facilitate axial sectioning and multiple scattering rejections. Referring to FIG. 1, an OCT system 100 includes a Michelson interferometer and a low coherence light source 110 (e.g., a broadband light source (BBS) such as a femtosecond laser or a superluminescent diode (SLD)). System 100 includes a beam splitter 120 which splits a light beam from source 110 into two beams, directing one of the beams (a reference beam) to a reference optic (e.g., an optical flat) 130 and directing the other beam to a sample 101, e.g., of biological tissue (sample beam). The part of the system that directs the sample beam to and from sample 101 is referred to as the sample arm, while the part of the system that directs the reference beam to and from the reference optic 130 is referred to as the reference arm. An objective lens 160 is positioned in the sample beam, focusing the sample beam to a spot at sample 101. Light reflected from reference optic 130 and sample 101 are recombined at beam splitter 120 and directed to a detector 140 e.g., a photodiode. Detector 140 is in communication with an electronics module 150 (e.g., a computer and/or other electronic signal processing equipment), which receives an electrical interference signal from detector 140 that corresponds to the intensity of the detected light. A Cartesian co-ordinate system is provided for reference.

As broadband light has a short coherence length, $L_c$, mathematically approximated by, $$L_c = (2 \ln 2/\pi) \cdot (\lambda^2/\Delta\lambda) \quad (1)$$

where $\lambda$, $\Delta\lambda$ are the central wavelength and the full-width-half-maximum (FWHM) spectral bandwidth of source 110, respectively. Referring to FIG. 2, the recombined light fields from the sample and the reference arms, $E_s$ and $E_r$, will coherently interfere only when their pathlength difference $\Delta L$ is matched to within the source coherence length, e.g., $L_c \approx 1$-15 μm, which defines the axial resolution ($\Delta z$) of system 100. Thus, in embodiments where an ultra broadband source such as a Ti:Al$_2$O$_3$ fs laser (e.g., central wavelength $\lambda = 800$ nm, $\Delta\lambda = 150$ nm) is used, $L_c \approx 2.4$ um in free space and 1.8 μm in soft tissue (assuming a refractive index of soft tissue of 1.38), ultrahigh-resolution OCT (uOCT) can be achieved which, theoretically, provides sufficient axial resolution to resolve subcellular details (the nuclear size of many normal epithelial cells, for example, is $\phi_N \approx 6$-8 μm, and of neoplastic cells, as another example, can increase to $\phi_N \approx 10$-20 μm).

When a biological tissue is placed in the sample arm, scanning $L_r$, e.g., by moving the reference optics to shorten or lengthen the path length of the reference beam, permits detection of an interferometric signal sequence from reflective or scattering interfaces in the sample at different depths along the z-axis.

Additional scanning of the sample beam in the transverse (e.g., x and/or y) directions allows for 2D (x-z) and even 3D (x/y-z) cross-sectional OCT imaging. Thus, the lateral resolution ($\Lambda_{OCT}$) of OCT depends on the focal spot size of the beam at sample 101. Under diffraction limit determined by the numerical aperture (NA) of objective lens 160, $$\Lambda = 2\lambda/\pi NA \quad (2)$$

where $NA = \phi/2f$, $\phi$ is waist diameter of the Gaussian beam and f is focal length. Because $\Delta z$ of OCT is directly related to $L_c$ (i.e., the laser source spectral bandwidth), this can circumvent the need for a bulky high-NA microscopic objective and focal tracking (z-scan) to obtain high axial resolution imaging. Accordingly, OCT can be suitable for endoscopic uses.

In general, a variety of detection schemes can be used. For example, in some embodiments, heterodyne detection can be used. Heterodyne detection typically involves introducing a shift, $f_D$, between the frequency of the reference light and the sample light. The result is a beat frequency corresponding to $f_D$ in the combined reference and sample light. The phase of the beat frequency corresponds to the optical path length difference between the reference and sample light paths. In certain embodiments, homodyne detection can be used.

In some embodiments, the interference signal can be filtered prior to signal processing to obtain phase information. For example, in embodiments where heterodyne detection is used, the signal can be filtered using a band pass filter centered on $f_D$.

The signal from detector 140 can be amplified prior to processing in electronics module 150. In some embodiments, the signal is amplified using a non-linear (e.g., logarithmic) scale. Alternatively, in certain embodiments, the signal can be amplified using a linear scale. Amplification using a linear scale can be advantageous as noise in the signal is amplified equally at all frequencies, whereas in implementations that use a non-linear scale can result in enhanced noise, ultimately manifesting as a broadened apparent coherence length or axial resolution. For example, a logarithmic scale can result in enhanced noise at low frequencies.

Because of the random nature (i.e., turbidity) of, e.g., bladder tissue (as an example of biological tissue), the detected OCT signal may include single-, least-backscattered light from the top urothelial cells and multiple-scattered light from the underlying high-scattering lamina propria or muscularis, which can be analyzed based on the relationship:

$$I_{OCT}(\Delta L_r) = 2\sqrt{I_s I_r}[\sqrt{R(L_s)} \otimes C(L_s)] \quad (3)$$

where $C(L_s) = \exp[-4(L_s/L_c)2] \cos kL_s$ is defined as the transfer function of OCT, and $R(L_s)$ is the pathlength resolved reflectance of the biological (e.g., bladder) tissue. Based on analysis of Eq. (3) and experiments, it is believed that due to multiple scattering of tissue, the effective imaging depth of OCT is limited to about 6~8 mean-free-paths or about 2-3 mm. Moreover, OCT shows tissue morphology as a distribution of intrinsic cellular backscattering or refractive-index variations.

In embodiments, time-lapsed frame averaging, termed as time-lapse uOCT or TL-uOCT can be used. Time-lapsed frame averaging refers to averaging multiple frames acquired at different times to provide a final image. In general, frames are separated by a time lapse, $\tau$. Typically, the time lapse between successive frames is the same, corresponding to the frame rate of the system, although in some embodiments, $\tau$ can vary between successive frames.

In some embodiments, $\tau$ is about 1 second or less (e.g., from about 0.5 seconds to about 0.03 seconds for a TD-OCT system). $\tau$ can be as short as about 30 milliseconds and even down to 3 milliseconds for a spectral domain (SD) OCT or frequency domain (FD) OCT system, e.g., using a swept source technique.

Averaging can be performed between successive frames or non-successive frames. For example, in some embodiments, averaging for each image can be performed over every other frame rather than over each successive frame.

Typically, the time lapse between frames is selected to provide an improved image relative to individual image frames. For example, the time-lapsed frame averaging can be configured to take advantage of the micro motion of living cells/tissue by selecting an appropriate value for $\tau$ and a suitable number of frames over which to perform the averaging. Without wishing to be bound by theory, it is believed that multiple scattering and speckle effects reduce the resolution of conventional uOCT below theoretical limits. For example, within an epithelial cell (e.g., having a diameter of approximately 20 μm), the nucleus is relatively large (e.g., having a diameter of approximately 6-8 μm), optically homogeneous, and has a low mismatch of refractive index ($\Delta n$) with surrounding cytoplasm. Thus, a nucleus favors forward scattering according to Mie's theory of scattering, resulting in a relatively low attribution to the detected OCT signal. Micro-organelles, however, which are typically smaller in size (e.g., having diameters less than about 1 μm) but have a higher $\Delta n$, tend to yield a higher backscattering, resulting in a relatively strong OCT signal. Unlike in other cells, such as large mesenchymal cells, for example, these cytoplasmic scatterers are densely packed in a small epithelial cell, thereby leading to enhanced intracellular multiple scattering and speckle noise that can eventually hide the subcellular details (e.g., nucleus) in an OCT image. Under such condition, Eq. (3) can be written as $$I_{uOCT}(L_r) = 2\sqrt{I_r} \left| \sum_i E^b(L_{s,i}) e^{-4[(L_{s,i}-L_r)/L_c]^2} \cdot \cos[k(L_{s,i} - L_r)] \right| \quad (4)$$

where $E^b(L_{s,i})$ refers to the backscattered light field within the focal volume with spot size $\Lambda$ and depth or coherence window of $\Delta z=(L_{s,j}-L_r)\leq L_c$. Here, i refers to a scatterer. The random phase interference among backscattering fields $\Sigma_i E^b(L_{s,i})\cos[k(L_{s,j}-L_r)]$ contributes to speckle noise. In other words, it is believed that subcellular imaging of epithelium may be restored if the speckle noise in uOCT can be effectively reduced. Speckle noise reduction can be reduced, for example, by time-lapsed frame averaging, if these scatterers move.

In certain embodiments, therefore, an appropriate time lapse, $\tau_{opt}$, should be selected to balance speckle reduction and deterioration of image resolution (e.g., caused by global motion or translation). It is believed that, if $\tau \ll \tau_{opt}$, there can be insufficient phase scrambling $\int k[L_{s,j}(\tau)-L_r]d\tau$ dr to suppress the speckle noise. However, where $\tau \gg \tau_{opt}$, tissue motion can wash away the subcellular details. In general, $\tau_{opt}$ is determined experimentally.

In some embodiments, $\tau_{opt}$ is in a range from about 0.1 s to 1 s. For example, in cases of ex vivo rat/mouse bladder studies, $\tau_{opt}$ has been found to be in a range from 0.4 s to about 1 s depending on the physiological conditions of the fresh specimens and even the type of species (e.g., Fisher rats moved faster than Sprague Dawley rats). In certain embodiments, $\tau_{opt}$ can be in a range from about 0.1 seconds to about 0.4 seconds. For example, in vivo samples $\tau_{opt}$ may be shorter than in ex vivo samples.

Because frame averaging relies on micromotion in a tissue sample to reduce speckle, living tissue samples or any tissue samples that move or are subjected to motion can be used. Accordingly, in certain embodiments, uOCT measurements are performed within relatively short time periods after harvesting the tissue (e.g., from a human). For example, uOCT measurements can be performed within 10 minutes of harvesting the tissue sample. Standard tissue preservation and/or culturing methods can be used (e.g., a tissue sample can be placed in Ringer's solution and maintained at a temperature from 36° C.-39° C., such as about 37° C.) to preserve physiological viability or some function. In some embodiments, uOCT measurements are performed in vivo.

Frame averaging can be performed in real time as the images are acquired and image registration is often required to minimize motion artifact (i.e., global trabslation rather than intracellular micromotion). Alternatively, or additionally, frame averaging can be performed at some later time after the acquisition of the individual image frames.

Proper frame averaging can maintain high image resolution. For example, for an uOCT system with lateral resolution (i.e., in the x-y plane) of 3 µm or less and axial resolution can be about 1.8 µm. The speckle reduction techniques discussed above can increase axial resolution relative to a conventional system (e.g., that does not utilize the speckle reduction techniques).

Referring to FIG. 3A, an embodiment of a time-domain uOCT system 200 includes a KLM Ti:Sapphire laser 210 (e.g., a KLM Ti:Sapphire laser with $\lambda$=800 nm and $\Delta\lambda$=128 nm) configured to illuminate a wavelength-flattened broadband fiberoptic Michelson interferometer. The interferometer is composed of a 50:50 splitter/combiner which splits light from laser 210 into the reference arm and sample arm via fiber polarization controllers (FPCs) 222 and 224, respectively.

Light in the sample arm is collimated using a fiber optic collimator (CM) 226, which directs the collimated light to a servo mirror 230 via an adjustable wedge prism pair 228. Light from servo mirror 230 is focused onto sample 101 by an objective lens 260.

By way of example, in certain embodiments, CM 326 collimates the light to have a diameter of approximately 5 mm. During operation, this light is scanned laterally by servo mirror 230 having a diameter of 8 mm. The scanned light is focused onto a sample, e.g., bladder tissue, surface using a commercial-grade f/10 mm achromatic lens to yield a focal spot size (lateral resolution) of $\Lambda \approx 3$ µm (Low NA, NA=0.25) based on ZEMAX modeling.

Light in the reference arm is directed to a rapid scanning optical delay (RSOD) 270, which includes a fiber optic collimator 278, a grating 276, an objective lens 274, and a reference mirror 372. Light is collimated using CM 278, and directed to grating 276, which reflects the light towards mirror 272. As an example, in embodiments collimated by CM 278 to a diameter of approximately 2 mm, attenuated and connected to RSOD 270 which is a grating-lens-based RSOD (e.g., which grating 276 having grating constant $d^{-1}$=1200/mm and lens 274 having f=80 mm) for axial scanning at a stable Doppler frequency shift ($f_D$=800 kHz) for heterodyne detection.

The light beams from both the sample and reference arms are recombined at splitter/combiner 220 and directed through a detection fiber and directed to a photodiode detector (PD) 240. The detected interferometric signal is bandpass filtered at $f_D$, amplitude linearly demodulated (set for partial demodulation to expedite phase scrambling), and digitized, e.g., via a 5 MHz, 12 bit A/D for 2D (up to 8 fps) and 3D uOCT image reconstruction. The system also includes an optical spectrum analyzer (OSA) 242, which also receives a portion of the light from the detection fiber via a 95:5 splitter 244.

Both PD 240 and OSA 242 are connected to a personal computer (PC) 250. PD 240 interfaces with PC 250 via an envelope detection module 255 (e.g., a full-wave rectifier followed by a low-pass filter with cut-off frequency at 300 kHz or 600 kHz to preserve some ripples for enhanced speckle phase scrambling) and OSA 242 interfaces with PC 250 via an interface board (GPIB) 258.

In system 200, dispersion compensation and ultra broadband propagation (e.g., chromatic aberration) are implemented separately. Mismatch of dispersions, e.g., group velocity dispersion (GVD) and 3rd-order dispersion (TOD) between the sample and reference arms is compensated by RSOD 270 (e.g., by adjusting the position of the grating an amount "b") in combination with adjustable wedge prism pair 228 (having prism depth D), formed from BK7, for example.

Chromatic aberration (e.g., introduced by objective 260 and RSOD 270) can reduce effective spectral bandwidth and thus axial resolution. The effects of chromatic aberration can be mitigated by increasing (e.g., maximizing) the detected cross spectrum, $S_{sr}(\lambda)$. $S_{sr}(\lambda)$ is given by $[S_s(\lambda) \cdot S_r(\lambda)]^{1/2}$, where $S_s(\lambda)$ is the spectrum of the sample light and $S_r(\lambda)$ is the spectrum of the reference light. The detected cross spectrum can be monitored by using OSA 242 interfaced with PC 250 to monitor changes in $S_{sr}(\lambda)$ and the cross-correlation function whose FWHM bandwidth determines the transform-limited axial resolution (here, "transform limit" means under the condition that the dispersion mismatch is fully compensated). Spectral reshaping can then be implemented by adjusting chromatic aberration (i.e., $\Delta f$) in RSOD 270 to optimize axial resolution with OSA 242 instantaneously.

Referring to FIG. 3B, spectral data from the example system described in connection with FIG. 3A indicates that due to uncorrected chromatic aberrations, both $S_s(\lambda)$ and $S_r(\lambda)$ can be narrower than the source spectrum $S_i(\lambda)$, e.g., $S_s(\lambda)$ is peaked at $\lambda>800$ nm. But, $S_r(\lambda)$ can be adjusted by $\Delta f$ to maximize at $\lambda<800$ nm so as to broaden $S_{sr}(\lambda)$ to $\Delta\lambda=155$ nm—thus exceeding the source $Si(\lambda)$ bandwidth, $\Delta\lambda=128$ nm. In FIG. 3B, $\Delta\lambda_s=113$ nm and $\Delta\lambda_r=62$ nm. Consequently, with reference to FIG. 3C, the measured axial resolution, $\Delta z$, is narrower than the source coherence length, for example, in the current configuration, $\Delta z=2.39$ μm<$L_c=2.95$ μm in air or $\Delta z<1.8$ μm in bladder tissue (where refractive index n≈1.38). Moreover, the two major side lobes with over 38% of peak power are reduced to <18% due to improved spectral shape. It is believed that $S_s(\lambda)$, to some extent, affects the speckle size—a broader $S_s(\lambda)$ leads to smaller speckle sizes. So, a strategy can be to maximize $S_s(\lambda)$ and then mitigate $S_r(\lambda)$ to yield a broad $S_{sr}(\lambda)$.

In some embodiments, uOCT can be implemented using an endoscope. Referring to FIG. 4, an example of an endoscope 300 for uOCT use includes an imaging fiber 310 and eyepiece lens 320 for visual guidance and a fiber 330 and optics module 340 for delivering and collecting the sample light for simultaneous uOCT imaging. Imaging fiber 310, fiber 330 and optics module 340 are housing in a sheath 301 (e.g., a rigid or flexible sheath). Optics module 340 includes optical elements configured to laterally scan the sample light over an area of the sample. Optics module 340 should be contained within a slender sheath (e.g., having a diameter of about 5 mm or less) and support a relatively high numerical aperture (NA) microendoscope (e.g., NA of about 0.25 or more) to enable a beam focus of to a small spot (e.g., $\Lambda\leq 3$ μm) thereby providing high lateral resolution.

Referring to FIGS. 5A-5F, two different optics modules are shown for endoscopic use. Both utilize MEMS mirrors to laterally scan the position of the sample light.

Figure 5A:
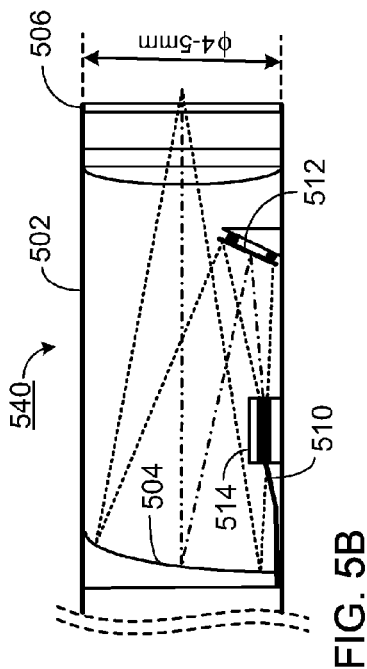
FIG. 5A-5C are a schematic diagram, an optical modeling diagram, and a modeled point spread function (in the transverse direction), respectively, for an embodiment of an optics module for delivery of sample light to a sample using an endoscope.

The configuration shown in FIG. 5A includes an endoscope 440 that houses a self-focusing lens 412 (e.g., a graded index lens) which collimates the sample light exiting a single mode fiber 410, e.g., to a diameter of approximately 2 mm. A reflecting prism 408 directs the light to a micro-electromechanical system (MEMS) mirror 416 (e.g., 2.1×2.0 mm$^2$) mounted on a ferrule 418. The optics module also includes an objective lens 404 (e.g., an achromat), which is tilted relative to the axis of the endoscopic sheath 402 housing the optical components. A window 414 is mounted at an end of sheath 402, protecting the optical components from debris and contamination while transmitting sample light. By contact with the tissue (e.g., bladder) surface, it ensures that the epithelium (top layer of tissue) is under focus.

Figure 5B:
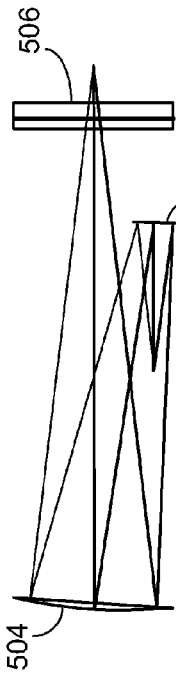
Figure 5C:
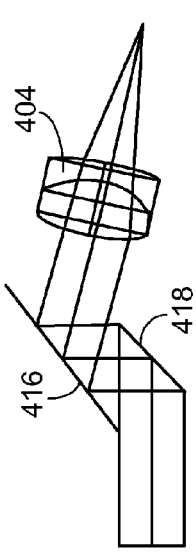
Figure 5D:
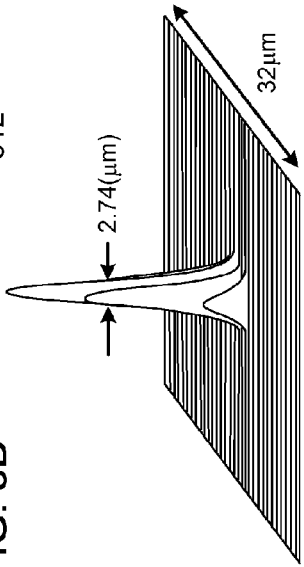
FIG. 5D-5F are a schematic diagram, a optical modeling diagram, and a modeled point spread function, respectively, for another embodiment of an optics module for delivery of sample light to a sample using an endoscope.

The configuration shown in FIG. 5D includes an endoscope 540 that also includes a MEMS mirror 512 (e.g., 1.2× 1.3 mm$^2$), which directs light from a fiber 510 (e.g., a single mode fiber) through an output coupler 514 towards a tilted focusing mirror 504 (e.g., focal length, f=9.04 mm). Tilted minor 504 directs the light to a plano-cylindrical lens 506 (e.g., f=6.21 mm). A window 508 seals the end of sheath 502.

In both configurations shown in FIGS. 5A and 5D, the MEMS mirror is configured to scan the light along a first axis providing a lateral scan for 2D imaging. The MEMS mirrors can also be actuated along a second axis, orthogonal to the first axis, which can allow for 3D imaging and/or alignment within the endoscope.

Figure 5E:
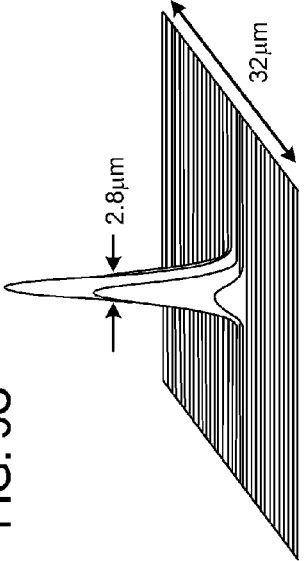

FIGS. 5B and 5E show the configurations of the optical modules shown in FIGS. 5A and 5D, respectively, as depicted by ZIMAX optical modeling software.

Figure 5F:
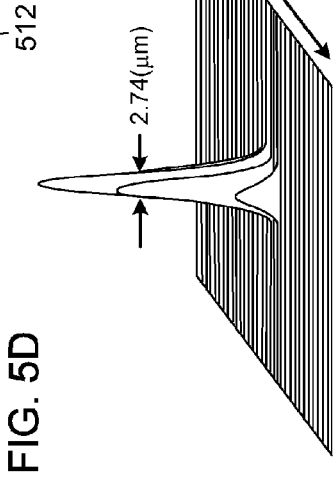

FIGS. 5C and 5F show the focus profiles or point-spread functions (PSFs) of ZIMAX simulations for the configurations shown in FIGS. 5A and 5D, respectively. The simulations show no spreading of PSF but an 11% and 14% drop over a lateral scan range of ±0.35 mm for the two designs. Other embodiments are also possible.

A potential problem involved in applying TL-uOCT (frame averaging) during in vivo endoscopic study, for example, can be motion-induced artifacts (e.g., translation caused by hand-shaking or breathing or bladder contraction). Optics modules for use in endoscopes can be designed to place the focal plane relatively close (e.g., ~100 μm) outside the thin glass window (e.g., including hard antireflection coating). For example, the embodiments shown in FIGS. 5A and 5D include windows 414 and 508, respectively. This allows the operator to position endface of the endoscope in contact with the sample surface for μOCT imaging, allowing for stable positioning of the endoscope with respect to the sample to minimize motion artifact. It is believed that this motion for subcellular imaging acts like a phase shift for all the terms in Eq. 4 and is therefore cancelled in terms of phase scrambling that reduces speckles (i.e., it is the local relative phase change that reduces speckles). However, it can add a phase shift between all the terms between two time lapsed frames so should be compensated by image registration.

Figure 5G:
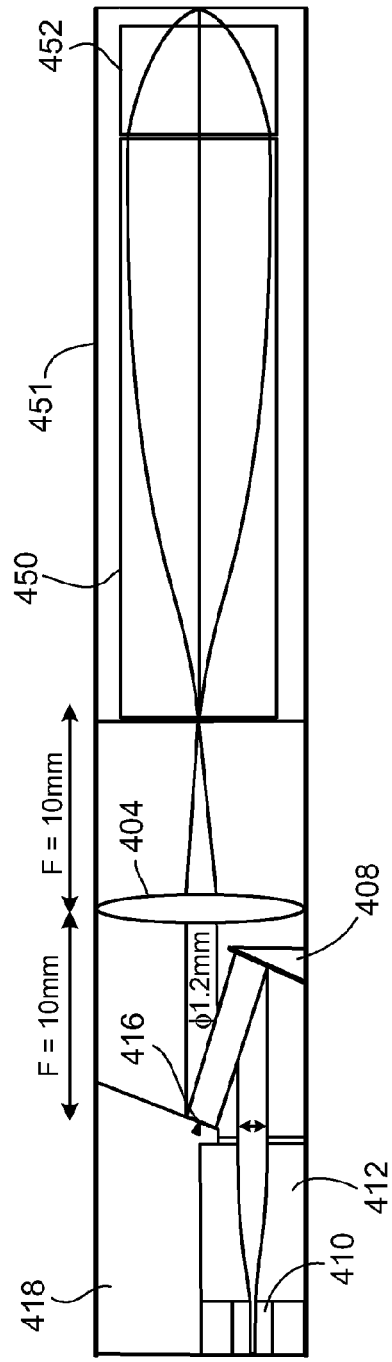
FIG. 5G-5H are schematic diagrams of the embodiments shown in FIG. 5A adapted to include graded index (GRIN) lenses.

In certain embodiments, the optics modules can be integrated with graded index (GRIN) lenses which permit a relatively low numerical aperture beam from the endoscope (e.g., NA of about 0.06) to be magnified by the lens to a high NA (e.g., 0.25 to 0.5) focused spot to be relayed to the sample in a small tube. For example, referring to FIG. 5G, in some embodiments, endoscope 440 is coupled to a tube 451 that includes a first GRIN lens 450 that collimates diverging light exiting the endoscope. Tube 451 also includes a second GRIN lens 452 that then focuses the collimated light to a spot at the distal end of tube 451. Here, the focused spot at the tube's distal end has a higher NA than the input to the tube from the endoscope. For example, the input can have an NA of about 0.06, while the final focused spot at the distal end has an NA in a range from 0.25 to 0.5.

Figure 5H:
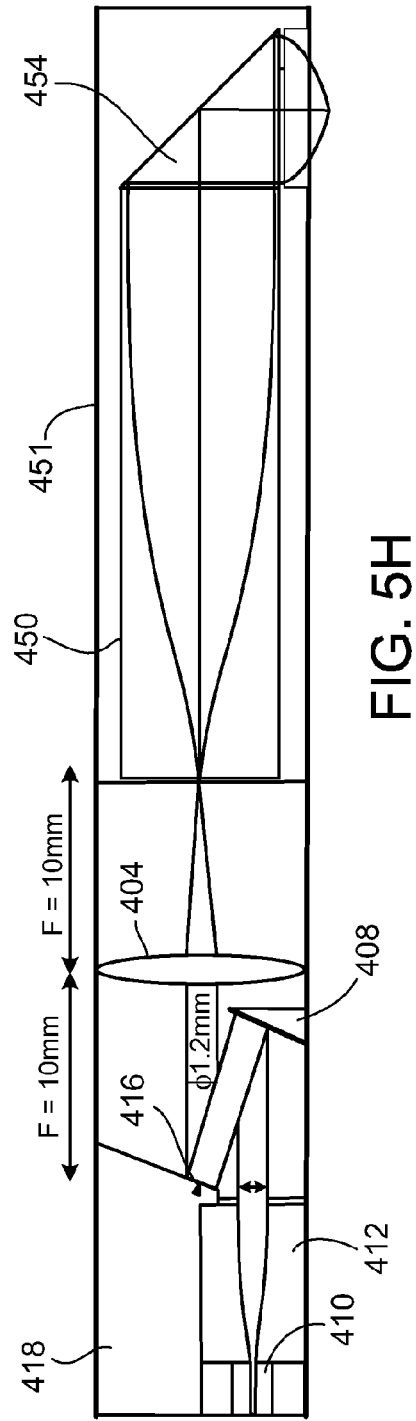

Referring to FIG. 5H, in some embodiments, the path of the light can be folded in tube 451 so that the focused spot is at a location on the side of tube 451, as opposed to being at its distal end. To accomplish this, tube 451 can include a folding optic 454 (e.g., a prism or mirror). After redirection by folding optic 454, the light is focused to a spot by second GRIM lens 456. As shown here, folding optic 454 is positioned in a portion of the light path where the light is collimated (i.e., between lens 450 and lens 456).

While the foregoing embodiments utilize an endoscope for in vivo study, other embodiments are also possible. For example, in some embodiments, a needle (e.g., a syringe needle) can be used for delivering the sample light to a tissue sample. FIG. 13A shows an example of such an embodiment. Here, a uOCT system 600 includes laser 310 (e.g., a Ti:Al2O3 laser, with $\lambda=800$ nm and $\Delta\lambda=128$ nm), 50/50 splitter/combiner 220, FPCs 222 and 224 (e.g., single mode FPCs), and a RSOD 670 in the reference arm. Output light from the interferometer is directed via splitter/combiner 220 to a spectral imager 655, which is in communication with a PC 350 that is configured to analyze collected data.

The sample arm of system 600 includes a lens 626 positioned to receive and collimate light exiting FPC 222. This collimated light is directed to a scanning mirror 630, which reflects the light through a scan lens 632, a tube lens 634, and objective lens, 636, and finally through a self-focusing relay lens 638 (e.g., a Selfoc GRIN lens) that is mounted in a needle 640. Lens 638 can have a diameter of 500 μm or less (e.g., 300

μm). Needle 640 can be a syringe needle. During use, needle 640 can be inserted into tissue to a depth of about 10-50 mm (e.g., about 20-30 mm).

Referring also to FIG. 13B, scanning mirror 630 can be a MEMS mirror configured to scan along two orthogonal directions (indicated by X and Y in FIG. 13B), providing data from a two dimensional (2D) area of a sample (which along with the depth scan provided by RSOD 670 provides a three dimensional (3D) scan of the sample).

A needle-based approach to delivering light to a sample can include many benefits. For example, such an approach can allow for deep tissue (e.g., pancreas, prostate, and/or brain tissue) subcellular imaging of nuclei using TL-μOCT, circumventing the need for fluorescence staining Deep tissue subcellular imaging of nuclei can allow for minimally-invasive optical biopsy for cancer grading (e.g., to track nuclear size increase), for example.

For en face imaging, a needle-based system can be used to permit laser speckle contrast imaging to extract subsurface microflow in the range facing the needle tip. En face imaging can be facilitated, for example, by replacing the laser scanning microscopy mode with full-field microscopy mode. This can be accomplished by removing the x-y scanning mirror, scan lens, and tube lens and placing a beam splitter in the position of the x-y scanning mirror and positioning a 2D CCD camera to detect the reflectance image.

While the foregoing embodiments are configured for time domain TL-uOCT, other implementations are also possible. For example, in some embodiments, spectral-domain TL-uOCT can be used. Spectral domain uOCT (SD-uOCT) can permit 2D and even 3D OCT imaging in real time. Based on spectral radar to reconstruct an axial-scan, SD-OCT can circumvent the need to mechanically scan the reference mirror conventionally done in TD-OCT.

A SD-uOCT system 700 is shown schematically in FIG. 6A. The system includes a broadband source (BBS) 710, a beamsplitter 740, a reference object 720 (e.g., a mirror), an objective lens 750 and a spectrometer 730. Beamsplitter 740 derives sample light and reference light from light from broadband source 710. The reference light is directed to reference object 720, while the sample light is directed through objective lens 750 to sample 101. Beamsplitter 740 also recombines measurement light and reference light reflected from sample 101 and reference 720, respectively, and directs the combined light to spectrometer 730.

As illustrated in FIG. 6B, at time t, a cell cluster within the focal zone (including cell 703 with nucleus 702 and organelles 701) include a group of scatterers providing back scattered fields $E_{bi}$ and pathlengths $L_{s,i} = L_{s0} + \Delta L_{s,i}$ are shown (i=1-4). Referring to FIG. 6C, at time t+τ, the same cell cluster is translated by $\Delta L_{s0}$. This translation can be compensated, for example, by image registration. The position change of organelles (e.g., organelles 701) is $\Delta L_i$ (i=1, 2, . . . ) causes a change of their relative pathlengths and thus phase scrambling. Therefore, if averaged, it will reduce speckle noise and uncover the nuclei.

Mathematically, a snapshot uOCT signal (e.g., A-scan or depth profile) at time t can be written as:

$$I_{uOCT}(L_r, t) = 2\sqrt{I_r}\left[\sum_i E^b(L_{s,i}(t))e^{-4(L_{s,i}(t)-L_r)^2/L_c^2}\cos[k(L_{s,i}(t)-L_r)]\right] \quad (5)$$

The pathlength of an intracellular organelle i can be expressed as $L_{s,i}(t) = L_{s0}(t) + \Delta L_{s,i}(t)$ to analyze the effects of two types of motion on speckle dynamics. Here, $L_{s0}$ is assigned as the origin of the coordinates which can be the center of a nucleus under focus. The motion of $L_{s0}$ pertains to translation of cell matrix (tissue), e.g., from $L_{s0}$ at time t in upper panel to $L_{s0} + \Delta L_{s0}$ at t+τ in FIG. 6C. $\Delta L_{s0}$ can be compensated by reference (i.e., change $L_r$ to $L_r + \Delta L_{s0}$) or by image registration and might otherwise blur the τ-lapse averaged image. Therefore, in this formalism, the translation of $L_r$ does not affect the speckle phase (i.e., pattern).

$\Delta L_{s,i}(t)$, which is attributed to intracellular relative motion of living cells, is important to TL-uOCT. Intracellular motion over time ti scrambles the phase $k\Delta L_{s,i}(\tau)$ (i=1, . . . , N), thus the TL-uOCT signal can be expressed by averaging several time-lapse snapshot uOCT signals of $I_{uOCT}(L_r)$ in Eq. (5) as, $$I_{TL-uOCT}(L_r) = \sum_\tau I_{uOCT}(L_r(t))/N_\tau = \quad (6)$$

$$(1/N_\tau)\sum_\tau 2I_r^{1/2} \sum_i E^b(L_{s,i}(t))e^{-4(L_{s,i}(t)-L_r)^2/L_c^2}\cos[k(L_{s,i}(t)-L_r)]$$

where $N_\tau$ is the number of τ-delayed averaging. The relative positions of $\Delta L_{s,i}(t+\tau)$ after time lapse τ shown in FIG. 6C are different from their counterparts $\Delta L_{s,i}(t)$ in FIG. 6B. After $L_{s0}$ is compensated, the summation $\Sigma_\tau I_{uOCT}(L_r)$ over sufficiently scrambled phases can minimize the speckle noise and thus uncover subcellular image.

In embodiments, $L_{s0}$ may not be completely compensated by image registration (e.g., where nuclei move in and out of imaging plane); therefore, a proper time lapse $\tau_{opt}$ (e.g., τ≈0.1-0.7 seconds) can be a compromise between image blurring (caused by uncompensated $\Delta L_{s0}$, therefore a shorter τ is more beneficiary) and sufficient phase scrambling (for which a longer τ is preferred) for effective speckle noise reduction. if τ<<$\tau_{opt}$, there is no sufficient phase scrambling $\int k[\Delta L_{s,i}(\tau)]$ dτ to suppress the speckle noise; if τ>>$\tau_{opt}$, tissue motion might wash away the subcellular details.

Figure 6D:
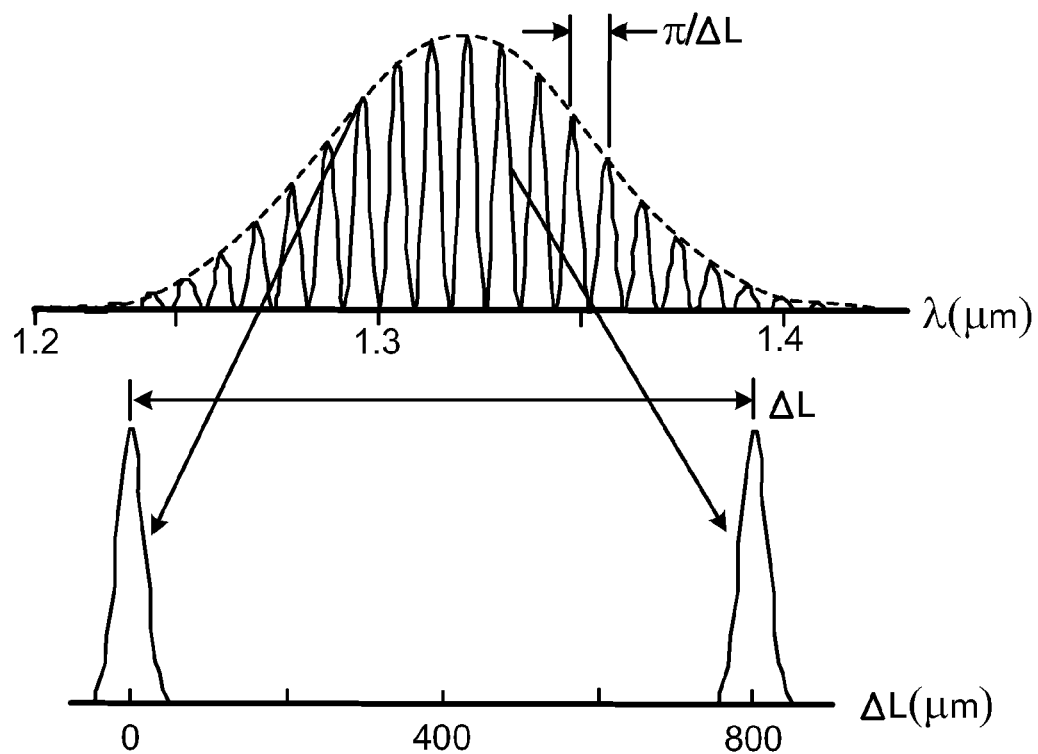
FIG. 6D are plots of a detected spectral intensity pattern for Spectral Domain (SD) Optical Coherence Tomography (OCT) system.

Referring to FIG. 6D, the detected spectral interference signal $I_{OCT}(\lambda, \Delta L)$, can also be written as:

$$I_{OCT}(\lambda, \Delta\lambda) = S(\lambda)[(I_s + I_r) + 2\sqrt{I_s I_r}\cdot\cos(2\pi\Delta L/\lambda)] \quad (7)$$

where $S(\lambda)$ is the source spectrum, $(I_s+I_r)$ is the DC intensity that contributes to the spectral envelope (i.e., the dashed curve in FIG. 6D) and the autocorrelation curve (dark curve in FIG. 6D) at $\Delta L=0$. The 2nd term $\cos(2\pi\Delta L/\lambda)$ modulates the spectral graph with a spectral frequency of $k=\pi/\Delta L$ (where $k=2\pi/\lambda$ is wave number). In other words, the depth-dependent reflection $R^{1/2}(\Delta L)$ encodes the spectrograph at different frequencies $k=\pi/\Delta L$, and can thus be decoded by an inverse frequency transform (e.g., an inverse Fast Fourier Transform (FFT)). According to FFT theorem, $L_c$ of SD-OCT is determined by the spectral bandwidth $S(\lambda)$, i.e., the same as TD-OCT as given by Eq. (1).

Figure 7:
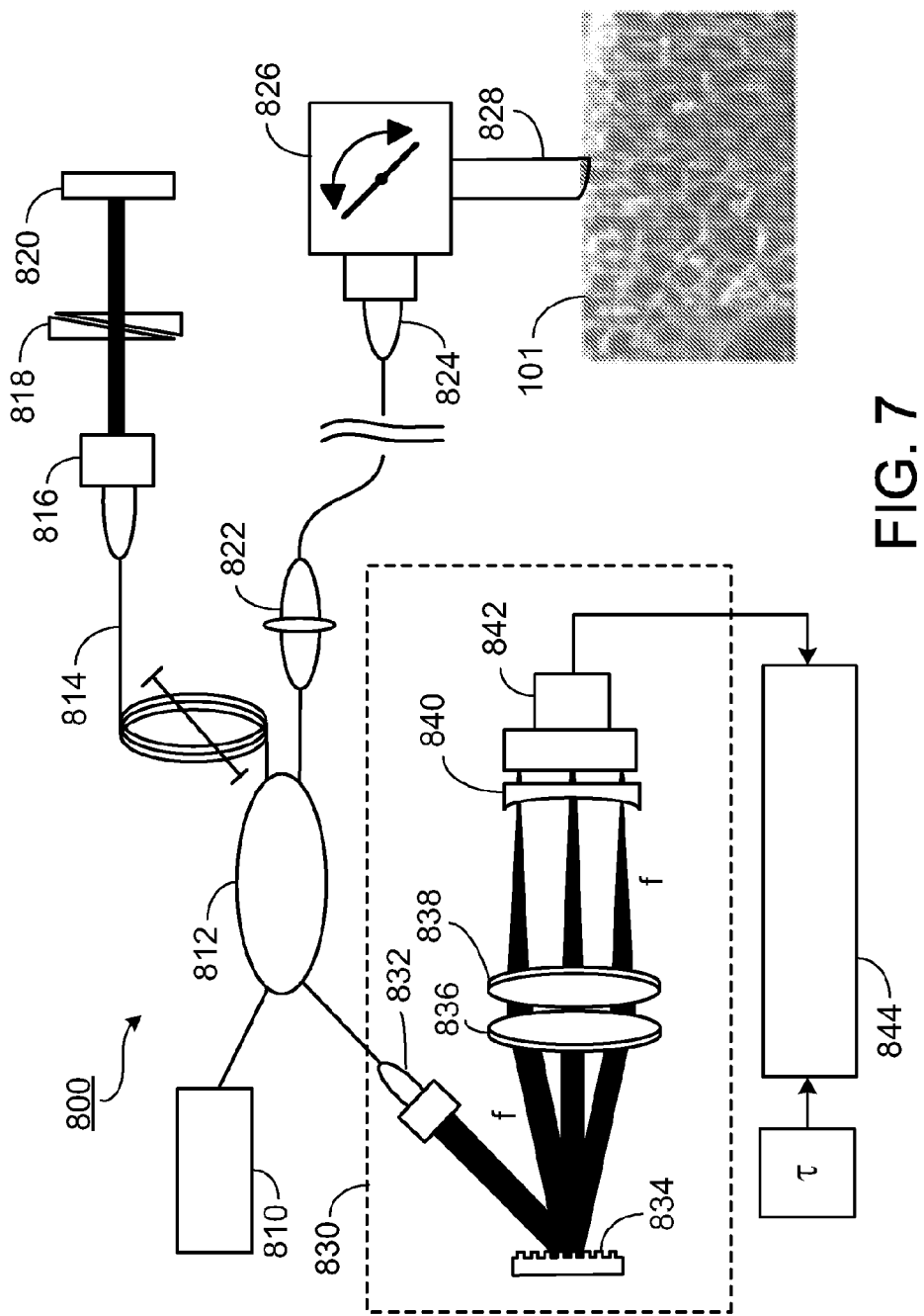
FIG. 7 is a schematic diagram of an embodiment of a SD TL-uOCT system.

A more detailed embodiment of a SD-uOCT system is shown in FIG. 7. SD-uOCT system 800 includes a broadband source 810 (e.g., an ultra broadband laser, e.g., with a central wavelength of 800 nm and a Δλ of 128 nm), which delivers light via a 50:50 splitter/combiner 812 to a reference arm and a sample arm of an interferometer. The reference arm includes a fiber polarization controller 814, a collimator 816, a wedge prism pair 818 and a reference mirror 820.

The sample arm includes a FC/APC fiber connector 822, a collimator 824, and a servo mirror 826 mounted in an endoscope 828. 50:50 splitter/combiner 812 also combines light returning from reference minor 820 and sample 101 and directs it to a spectral imaging assembly 830, which includes a collimator 832 (e.g., an achromatic collimator), which directs the light to a grating 834 (e.g., having a 1200/mm grating pitch) which disperses the incident light into component wavelengths. Grating 834 reflects the light to a telecentric lens system (including lenses 836, 838, and 840) for field correction. The lens system focuses the dispersed light onto a pixilated detector 842 (e.g., a CCD: 2048-pixel line camera via Camlink to PC for high-speed ultrahigh-resolution spectral imaging). The three lens telecentric system (e.g., f=80 mm) can reduce field curvature at pixilated detector 842. In some embodiments, the system dynamic range can be 127 dB at up to 54 frames per second (e.g., with 0.8 mW incident laser power—which is under ANSI Laser Safety Standards). Lenses 836, 838, and 840 can facilitate high spectral resolution imaging across the entire pixels of camera 842, which can allow SD-µOCT to maintain high image contrast along a larger field of depth than lens system without effective field correction.

In certain embodiments, SD-uOCT can be used to perform 2D uOCT at, e.g., 30-54 frames/s. Multiple SD-uOCT frames can be averaged allowing time-lapse uOCT to be performed among frames with chosen time lapse, e.g., frame 1, frame 1+n, frame 1+n+n=1+2n, and frame 1+3n where n is related to time lapse. By performing image registration among these frames prior to frame averaging, motion artifacts (e.g., global motion induced by bladder shift or scope handshake, which is the not the same local micromotion—intracellular micromotion that attributes to speckle noise) can be reduced (e.g., minimized). This method may be advantageously used for in vivo imaging because it can allow time-lapse imaging where $\tau_{opt}$<0.1 second. Accordingly, it can be used to reduce (e.g., minimize/correct) global motion-induced artifact in vivo endoscopically.

Figure 12A:
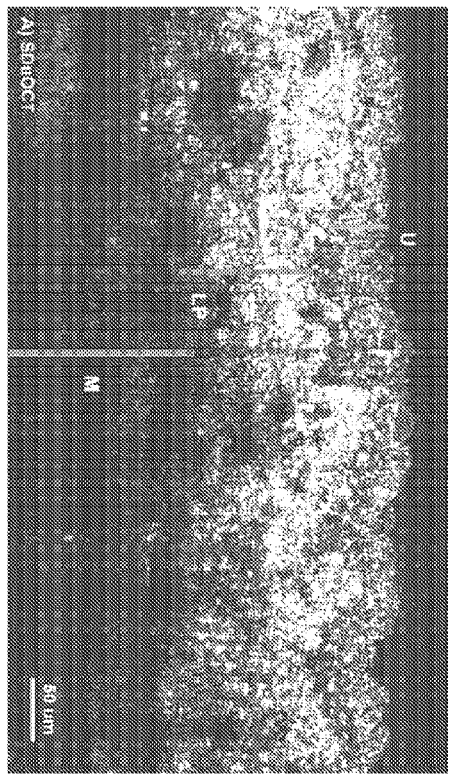
FIGS. 12A and 12B show a snap shot and time-lapse frame averaged image of a SD rat bladder using SD TL-uOCT.
Figure 12B:
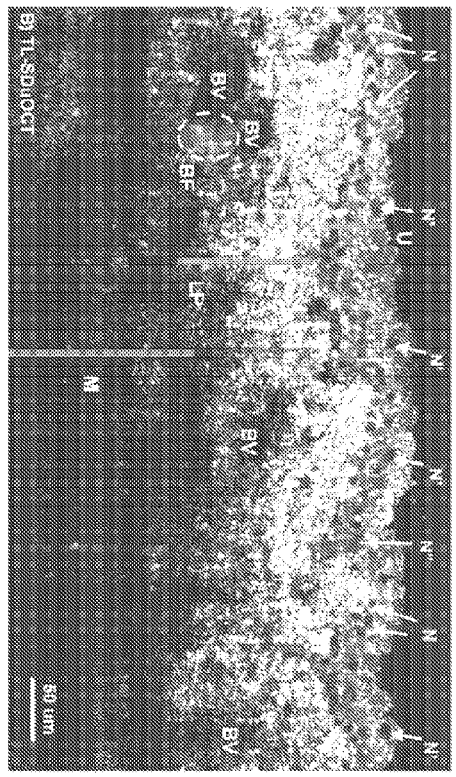

Referring to FIGS. 12A-B, this is exemplified in a snapshot (FIG. 12A) and time-lapsed frame averaged image (FIG. 12B) taken ex vivo of a SD rat bladder using TL-SD uOCT. The time-lapsed frame averaging was performed over 5 frames ($\tau \approx 0.1$ s). Labels are as follows: BV: bladder vessels, BF: residual blood flow (appeared blurring due to phase-resolved averaging). N: normal nuclei; N': umbrella cell nuclei.

Needle based systems can also be used for SD-OCT. In some embodiments, use of SD-OCT can permit simultaneous Doppler imaging of microflow (e.g., capillary flow) at relatively deep tissue ranges (e.g., at about 20 mm or more). Moreover, it can provide two-dimensional or three-dimensional cross-sectional flow imaging.

In general, OCT systems can also be integrated with other imaging techniques. For example, OCT systems (e.g., the needle-based system shown in FIG. 13A) can be integrated with a needle-lens-based one photon or two photon fluorescence imaging platform.

EXAMPLES

Figure 8A:
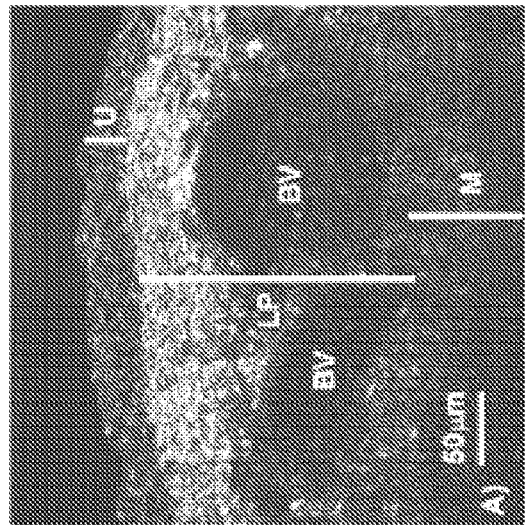
FIGS. 8A-8C is a single frame uOCT image, a time lapse frame averaged uOCT image, and a histological microscope image of a living rat bladder ex vivo.
Figure 8B:
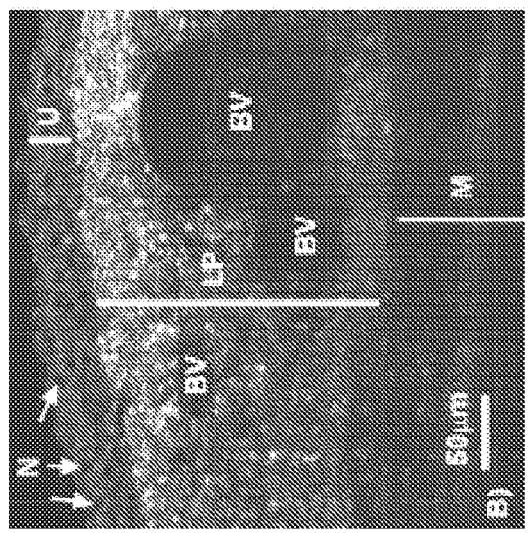
Figure 8C:
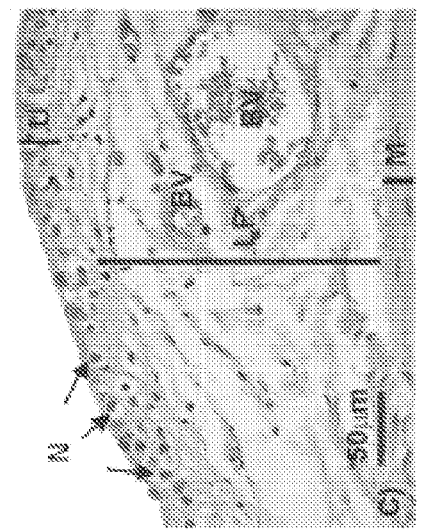

FIG. 8A-8C show subcellular images of living rat bladder ex vivo. Specifically, FIG. 8A shows a single uOCT frame, FIG. 8B shows a time-lapse dynamic frame averaged uOCT image, and FIG. 8C shows a corresponding histological slide. Features of these images are identified using the following labels: urothelium—U; lamina proppia—LP; upper muscularis—M; blood vessel—BV; urothelial nucleus—N. The uOCT images were acquired using a commercial grade single achromatic lens (f/10 mm, NA/~0.25) which provided a cross-sectional image over 0.6 mm of depth without focus tracking. For FIG. 8B, 4-frame averaging with $\tau_{opt} \approx 0.4$ s time lapse was used. As apparent in FIG. 8A, the single uOCT frame shows no cellular contrast in the urothelium, whereas frame averaging clearly uncovers the epithelial nuclei (N) as is apparent in FIG. 8B. The TL-uOCT measurement of urothelial nuclear size, 7.9±1.4 µm, closely matches the histological evaluation, 7.2±0.8 µm. The nuclei appeared echolow in the surrounding high-scattering background.

Referring to FIGS. 9A-9C, as a further example, ex vivo studies using SV40-T mice (a transgenic model for orthotropic CIS) were performed. Here, uOCT images were obtained by averaging four individual frames with $\tau_{opt}$ of approx. 0.7 s. Corresponding histological images are shown in FIGS. 10A-10C. FIGS. 9A and 10A show normal bladder tissue with nuclear size as calculated from the uOCT (histological) image of N≈6.6±1.2 µm (5.8±0.9 µm). FIGS. 9B and 10B show bladder tissue displaying low-grade TCC with average nuclear size of 5.4±0.6 µm calculated from the histological image (For this lesion, subcellular details diminished due to high density and smaller size of nuclei). FIGS. 9C and 10C show bladder tissue with high grade TCC. Here, average nuclear size was measured using uOCT (histology) as N"≈13.4±1.3 µm (12.9±0.9 µm). Individual sizes of the nuclei identified in the figures were $N_1$"=13.7 µm (12.1 µm), $N_2$"=15.0 µm (13.7 µm), $N_3$"=13.4 µm (10.9 µm), $N_4$"=12.7 µm (14.6 µm), $N_5$"=14.1 µm (15.1 µm) as measured using uOCT (histology). Other symbols used in the images are the same as those used for FIGS. 8A-8C.

Figures 11A, 11B:
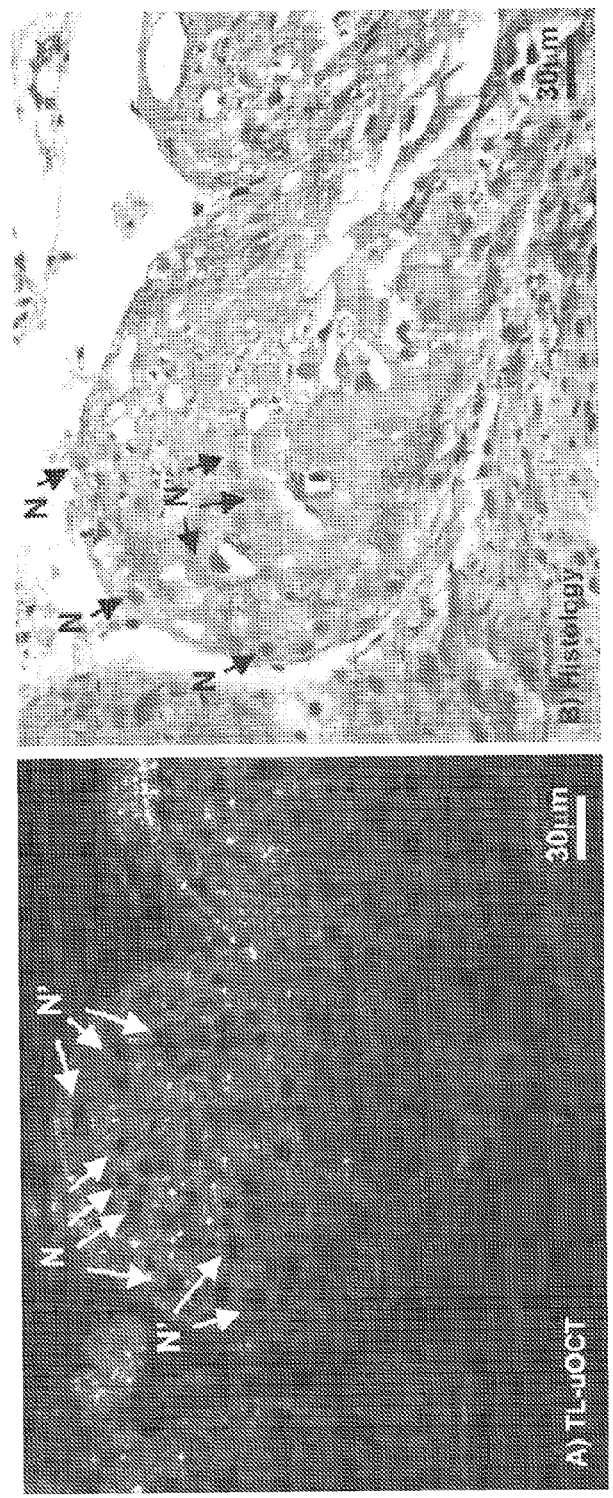
FIGS. 11A and 11B show ex vivo TL-uOCT and histological sections, respectively, of SV40-T mouse bladder.

FIGS. 11A and 11B show ex vivo TL-uOCT and histological sections, respectively, of SV40-T mouse bladder. FIG. 11A shows time-lapse frame averaging which was performed over 4 frames ($\tau \approx 0.6$ s). Bladder became papillary TCC (low-grade). Normal nuclear size measured by OCT/histology: $\phi_N$=(7.4±0.81) µm/$\phi_N$=(7.3±0.49) µm. Low-grade TCCs: $\phi_N$=(10-13) µm/$\phi_N$=(12-14) µm. Unlike that in FIG. 9B, which shows high density without enhanced nuclear size, this lesion showed enhanced nuclei and thus be resolved by TL-uOCT.

A number of embodiments have been disclosed. Other embodiments are in the claims.

What is claimed is:

1. A method, comprising:
    obtaining a tissue sample exhibiting intracellular motion;
    using an optical coherence tomography system to acquire a plurality of frames of the tissue sample, each frame comprising optical information about the composition of the sample through a section of the sample acquired over an acquisition interval t; and
    selecting a time lapse interval for averaging over at least two of the frames, such that the time lapse τ between the at least two frames is selected based on an extent of the intracellular motion of the tissue sample;
    wherein τ is sufficiently long to reduce speckle noise in images acquired using the optical coherence tomography system due to the intracellular motion, and sufficiently short to reduce image resolution deterioration in images acquired using the optical coherence tomography system; and
    averaging over the at least two frames to provide an image of the section of the sample.

2. The method of claim 1, wherein the averaging is over three or more frames to provide the image.

3. The method of claim 1, wherein the tissue sample is a living tissue sample while the frames are acquired.

4. The method of claim 1, wherein acquiring each frame comprises directing test radiation onto the sample, collecting test radiation scattered by the sample, and combining the collected test radiation with reference radiation, the test and reference radiation being produced by a common source.

5. The method of claim 4, wherein the common source comprises a laser.

6. The method of claim 4, wherein the common source comprises a light emitting diode.

7. The method of claim 4, wherein the test and reference radiation are directed along different paths prior to being combined, and an optical path length difference between at least some of the test and reference radiation is zero.

8. The method of claim 4, wherein the test and reference radiation is low-coherence radiation.

9. The method of claim 4, wherein the test and reference radiation is broadband radiation.

10. The method of claim 4, wherein directing the test radiation onto the sample comprises focusing the test radiation onto the sample.

11. The method of claim 4, wherein the test radiation is focused using an objective lens consisting of an achromatic doublet.

12. The method of claim 4, wherein the test and reference radiation are directed along the different paths using an interferometer.

13. The method of claim 12, wherein the interferometer is a Michelson interferometer.

14. The method of claim 4, wherein acquiring each frame comprises varying an optical path length of the reference radiation path.

15. The method of claim 14, wherein the optical path length of the test radiation is held constant while the optical path length of the reference radiation is varied.

16. The method of claim 14, wherein acquiring each frame comprises scanning the test radiation across a portion of the sample and varying the optical path length of the reference radiation path for each of a plurality of locations across the portion of the sample.

17. The method of claim 16, wherein the test radiation is scanned using a MEMS device.

18. The method of claim 4, wherein the test radiation is delivered to the sample using an endoscope.

19. The method of claim 1, wherein the sample is an in vivo sample.

20. The method of claim 19, wherein the in vivo sample is from a human subject.

21. The method of claim 1, wherein acquiring the frames comprises amplifying an interference signal corresponding to detected combined test and reference radiation, wherein the interference signal is amplified using a non-logarithmic scale.

22. The method of claim 21, wherein the non-logarithmic scale is a linear scale.

23. The method of claim 22, wherein the amplification using the linear-scale incompletely demodulates the interference signal so that there remains a modulation of the amplified interference signal sufficient to promote frame averaging to reduce speckle noise.

24. The method of claim 21, wherein the amplitude of the interference signal is amplified at a frequency, $f_D$, where $f_D$ is a heterodyne frequency between sample light and reference light of the optical coherence tomography system.

25. The method of claim 24, wherein the interference signal is filtered using a frequency bandpass filter that passes $f_D$ prior to amplification.

26. The method of claim 1, wherein the extent of intracellular motion is related to a time varying optical path length of light from the optical coherence tomography system to an intracellular structure undergoing the intracellular motion.

* * * * *

UNITED STATES PATENT AND TRADEMARK OFFICE
CERTIFICATE OF CORRECTION

PATENT NO. : 8,948,846 B2
APPLICATION NO. : 12/678377
DATED : February 3, 2015
INVENTOR(S) : Pan Page 1 of 1

It is certified that error appears in the above-identified patent and that said Letters Patent is hereby corrected as shown below:

In the specification

Column 1
Line 14, after the "CROSS-REFERENCE TO RELATED APPLICATIONS" section, insert

-- STATEMENT AS TO FEDERALLY SPONSORED RESEARCH

This invention was made with government support under grant number DK059265 awarded by the National Institute of Health. The government has certain rights in the invention. --

Signed and Sealed this
Fifth Day of May, 2015

Michelle K. Lee
*Director of the United States Patent and Trademark Office*